United States Patent
Kawabata et al.

(10) Patent No.: US 7,259,017 B2
(45) Date of Patent: Aug. 21, 2007

(54) METHOD OF DIAGNOSING LUBRICATED PORTION AND SYSTEM OF DIAGNOSING LUBRICATED PORTION

(75) Inventors: Masahiko Kawabata, Aichi-ken (JP); Yoshinori Sasaki, Aichi-ken (JP)

(73) Assignee: Tribotex Co., Ltd., Ohbu-shi (JP)

( * ) Notice: Subject to any disclaimer, the term of this patent is extended or adjusted under 35 U.S.C. 154(b) by 655 days.

(21) Appl. No.: 10/722,551

(22) Filed: Nov. 28, 2003

(65) Prior Publication Data

US 2005/0118063 A1 Jun. 2, 2005

(51) Int. Cl.
*G01N 33/26* (2006.01)
*G01N 1/18* (2006.01)

(52) U.S. Cl. ............ 436/60; 436/2; 436/171; 436/174; 436/177; 422/68.1; 422/82.05; 422/101; 356/70

(58) Field of Classification Search .......... 436/2, 436/60, 171, 174, 175, 177, 178, 73, 77, 436/79, 80, 81, 84; 422/68.1, 101, 82.05; 356/70
See application file for complete search history.

(56) References Cited

U.S. PATENT DOCUMENTS

| | | | | |
|---|---|---|---|---|
| 2,818,766 A | * | 1/1958 | Hutchinson | ........... 356/36 |
| 3,751,661 A | * | 8/1973 | Packer et al. | ........... 378/47 |
| 3,981,584 A | | 9/1976 | Guymer | |
| 4,169,677 A | * | 10/1979 | Luria | ........... 356/70 |
| 4,448,887 A | | 5/1984 | Kauffman et al. | |
| 5,408,306 A | * | 4/1995 | Anderson | ........... 356/36 |
| 5,504,573 A | * | 4/1996 | Cheiky-Zelina | ........... 356/70 |
| 5,586,161 A | | 12/1996 | Russell et al. | |
| 5,604,441 A | * | 2/1997 | Freese et al. | ........... 324/663 |
| 6,949,936 B2 | * | 9/2005 | Stone et al. | ........... 324/633 |

FOREIGN PATENT DOCUMENTS

| | | |
|---|---|---|
| GB | 1 345 682 | 1/1974 |
| JP | 10-206333 | 8/1998 |

* cited by examiner

*Primary Examiner*—Maureen M. Wallenhorst
(74) *Attorney, Agent, or Firm*—Oblon, Spivak, McClelland, Maier & Neustadt, P.C.

(57) ABSTRACT

The invention provides a method of diagnosing a lubricated portion which can precisely measure a metal concentration in a lubricating oil and can diagnose accurately a state of the lubricated portion on the basis of a value of measurement. In accordance with the present diagnosing method, a lubricating oil picked up from the lubricated portion is diluted by an organic solvent so as to prepare a sample oil, the sample oil is filtrated by a filter so as to separate a large-diameter metal particle having a particle diameter larger than 0.5 μm, a metal concentration of a solution formed by dissolving the large-diameter metal particle by an acid and a metal concentration of a filtrate including a small-diameter metal particle having a particle diameter equal to or smaller than 0.5 μm is measured in accordance with the inductively coupled plasma analysis, an wear depth in the lubricated portion is determined on the basis of the respective metal concentrations of the solution and the filtrate, and an wear state of the lubricated portion is diagnosed on the basis of a rate of change of the wear depth in accordance with a time elapse.

10 Claims, 5 Drawing Sheets

《DIAGNOSIS COMMENT WITH RESPECT TO
                         SLIDE BEARING PORTION》

・OVERHAUL TIMING : O/O/O
・FAILURE MODE : FATIGUE WEAR
・FAILURE REASON: VIBRATION AND OVERLOAD

METHOD OF DIAGNOSING LUBRICATED PORTION AND SYSTEM OF DIAGNOSING LUBRICATED PORTION

BACKGROUND OF THE INVENTION

1. Field of the Invention

The present invention relates to a method of diagnosing a lubricated portion and a system of diagnosing a lubricated portion, and more particularly, to a method of diagnosing a lubricated portion and a system of diagnosing a lubricated portion which can precisely measure a metal concentration in a lubricating oil and can diagnose accurately a state of the lubricated portion on the basis of a value of measurement.

2. Description of the Prior Art

Conventionally, as a method of diagnosing a lubricated portion, there has been known a so-called SOAP method (Spectrometric Oil Analysis Program), and this method is a method of diagnosing a state of the lubricated portion comprising the steps of diluting a lubricating oil picked up from the lubricated portion by an organic solvent so as to prepare a sample oil, exciting a metal particle in the sample oil by a plasma or the like so as to emit light, measuring a wavelength and a strength of an atomic spectrum line obtained by separating the light so as to measure the metal concentration, and diagnosing the state of the lubricated portion the basis of a rate of change of the metal concentration in accordance with a time elapse. In accordance with this method, there can be obtained an advantage that a state of lubrication and a state of wear can be easily diagnosed without disassembling and inspecting a structure in the lubricated portion.

However, in accordance with the conventional method of diagnosing the lubricated portion, in the case that a large-diameter metal particle having a particle diameter larger than 10 µm is contained in the picked-up lubricating oil, the large-diameter metal particle is not excited, so that it is impossible to measure an accurate value of the metal concentration in the lubricating oil. As a result, it is impossible to accurately diagnose the state of the lubricated portion. In other words, the conventional method of diagnosing the lubricated portion is only a rough standard for diagnosing a certain degree of state of the lubricated portion.

SUMMARY OF THE INVENTION

Accordingly, the present invention is made by taking the current status mentioned above into consideration, and an object of the present invention is to provide a method of diagnosing a lubricated portion and a system of diagnosing a lubricated portion which can precisely measure a metal concentration in a lubricating oil and can diagnose accurately a state of the lubricated portion on the basis of a value of measurement.

The invention will now be described following

[1]. A method of diagnosing a lubricated portion comprising the steps of:

filtrating a lubricating oil picked up from the lubricated portion so as to separate a large-diameter metal particle;

thereafter measuring a metal concentration of a solution formed by dissolving said large-diameter metal particle by an acid in accordance with an emission spectrometry and measuring a metal concentration of a filtrate in accordance with the emission spectrometry; and diagnosing a state of said lubricated portion on the basis of the respective metal concentrations of said solution and said filtrate.

[2]. A method of diagnosing a lubricated portion as mentioned in above [1], wherein the state of said lubricated portion is diagnosed by determining an wear depth in said lubricated portion from a total value of the respective metal concentrations of said solution and said filtrate, and on the basis of a rate of change of said wear depth in accordance with a time elapse.

[3]. A method of diagnosing a lubricated portion as mentioned in above [1] or [2], wherein said lubricating oil is filtrated by a filter having a hole diameter between 0.01 and 10.00 µm.

[4]. A method of diagnosing a lubricated portion as mentioned in any one of above [1] to [3], wherein said emission spectrometry is constituted by an analyzing method using an inductively coupled plasma.

[5]. A system of diagnosing a lubricated portion comprising:

a filtrating means for filtrating a lubricating oil picked up from the lubricated portion so as to separate a large-diameter metal particle;

an emission spectrometry means for measuring respective metal concentrations of a solution formed by dissolving said large-diameter metal particle by an acid and a filtrate;

a diagnosing means for diagnosing a state of said lubricated portion on the basis of the respective metal concentrations of said solution and said filtrate; and a display means for displaying a result of diagnosis of said diagnosing means.

[6]. A system of diagnosing a lubricated portion as mentioned in above [5], wherein the system of diagnosing a lubricated portion is provided with an wear depth calculating means for determining an wear depth in said lubricated portion from a total value of the respective metal concentrations of said solution and said filtrate, a memory means for storing the result of calculation by said wear depth calculating means, and a change rate calculating means for determining a rate of change of said wear depth in accordance with a time elapse from the result of calculation by said wear depth calculating means and the result of storage by said memory means, and said diagnosing means diagnosis the state of said lubricated portion on the basis of the result of calculation of said change rate calculating means.

[7]. A system of diagnosing a lubricated portion as mentioned in above [5] or [6], wherein said filtrating means includes a filter having a hole diameter between 0.01 and 10.00 µm.

[8]. A system of diagnosing a lubricated portion as mentioned in any one of above [5] to [7], wherein said emission spectrometry means is an emission spectrometry apparatus using an inductively coupled plasma.

In accordance with the method of diagnosing the lubricated portion on the basis of the present invention, even in the case that the large-diameter metal particle having the particle diameter larger than 10 µm is contained in the lubricating oil, it is possible to separate the large-diameter metal particle by filtrating the lubricating oil, and it is possible to measure the metal concentration of the solution in which the large-diameter metal particle is dissolved by the acid and measure the metal concentration of the filtrate in accordance with the emission spectrometry. Accordingly, it is possible to precisely measure the metal concentration in the lubricating oil. As a result, it is possible to accurately diagnose the state of the lubricated portion on the basis of the value of the metal concentration.

Further, in the case of determining the depth of wear in the lubricated portion on the basis of the metal concentration in the lubricating oil and diagnosing the state of the lubricated portion on the basis of the rate of change of the wear depth in accordance with the time elapse, it is possible to control the tendency of the wear depth precisely and it is possible to more accurately diagnose the state of the lubricated portion.

Further, in the case that the lubricating oil is filtrated by the filter having the hole diameter between 0.01 and 10.00 μm, it is possible to measure the metal concentration of the solution in which the large-diameter metal particle having the particle diameter larger than 0.01 to 10.00 μm is dissolved by the acid, and it is possible to measure the metal concentration including the small-diameter metal particle having the particle diameter equal to or smaller than 0.01 to 10.00 μm, in accordance with the emission spectrometry, so that it is possible to precisely measure the metal concentration in the lubricating oil.

Further, in the case of measuring the metal concentration of the metal particle in the lubricating oil in accordance with the emission spectrometry using the inductively coupled plasma, it is possible to more precisely measure the metal concentration in a little amount of lubricating oil.

In accordance with the system of diagnosing the lubricated portion of the present invention, it is possible to filtrate the lubricating oil by the filtrating means so as to separate the large-diameter metal particle, it is possible to measure the respective metal concentrations of the solution and the filtrate in which the large-diameter metal particle is dissolved by the acid, by the emission spectrometry means, it is possible to diagnose the lubricated portion on the basis of the respective metal concentrations of the solution and the filtrate by the diagnosing means, and it is possible to display the result of diagnoses by the displaying means. Accordingly, it is possible to accurately and automatically diagnose the state of the lubricated portion on the basis of the precise value of the metal concentration in the lubricating oil.

Further, in the case that the diagnosing means diagnoses the state of the lubricated portion on the basis of the rate of change of the wear depth in accordance with the time elapse, it is possible to precisely control the tendency of the wear depth, and it is possible to more accurately diagnose automatically the state of the lubricated portion.

Further, in the case that the filtrating means includes the filter having the hole diameter between 0.01 and 10.00 μm, it is possible to measure the metal concentration of the solution in which the large-diameter metal particle having the particle diameter larger than 0.01 to 10.00 μm is dissolved by the acid, and it is possible to measure the metal concentration including the small-diameter metal particle having the particle diameter equal to or smaller than 0.01 to 10.00 μm, in accordance with the emission spectrometry, so that it is possible to precisely measure the metal concentration in the lubricating oil.

Further, in the case of that the emission spectrometry means is the emission spectrometry apparatus using the inductively coupled plasma, it is possible to more precisely measure the metal concentration in a little amount of lubricating oil.

As the "lubricated portion" mentioned above, there can be listed up, for example, a slide bearing portion, a rolling bearing portion, a gear portion, a sliding portion and the like. The sliding portion may be constituted, for example, by a sliding portion of a contact point switching mechanism in a transformer. Accordingly, it is possible to accurately diagnose a state of the sliding portion of the contact point switching mechanism in the transformer. Further, as the "lubricating oil" mentioned above, there can be listed up, for example, a spindle oil, a machine oil, a dynamo oil, a turbine oil and the like corresponding to a petroleum lubricating oil.

Figure 4:
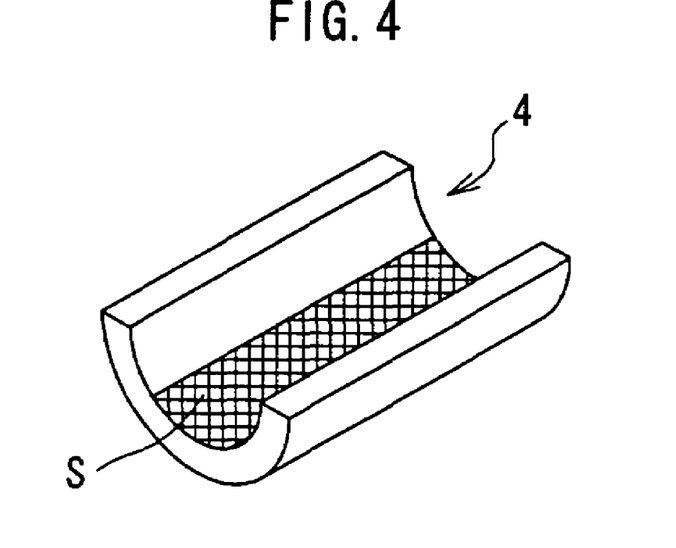
FIG. 4 is schematic views for explaining an wear depth (wear area) of a sliding bearing portion.

Further, the lubricating oil mentioned above can be constituted, for example, by a semisolid grease. Further, the lubricating oil picked up from the lubricated portion is normally diluted by an organic solvent so as to form a sample oil, and the large-diameter metal particle is separated by filtrating the sample oil. Further, the "large-diameter metal particle" mentioned above is structured, for example, such that the particle diameter thereof has a diameter which is preferably larger than 0.01 to 10.00 μm (more preferably, 0.05 to 5.00 μm, further preferably 0.07 to 3.00 μm, and particularly preferably 0.10 to 1.00 μm). Further, the "filtrate" mentioned above normally includes a small-diameter metal particle, a dissolved metal, a metal additive agent and the like having a particle diameter smaller than the large-diameter metal particle mentioned above. Further, the "state of the lubricated portion" mentioned above may be, for example, a lubricating state and/or a wear state of the lubricated portion. Further, the "diagnosing the state of the lubricated portion" mentioned above may mean, for example, estimating an wear aspect (a failure mode) in the lubricated portion such as an adhesive wear, an abrasive wear (a cutting wear), a fatigue wear or the like. Further, it can mean estimating a cause of generation in correspondence to the wear aspect mentioned above in the lubricated portion, for example, a lack of oil film generating the adhesive wear, an external mixing foreign material and an wear particle generating the abrasive wear, a vibration and an overload generating the fatigue wear, and the like. Further, for example, it may mean estimating a countermeasure for an abnormality such as a lubricating oil filtration, an additive agent input, an additional oil, a shutdown, an overhaul, a parts replacement and the like. Further, it may mean forecasting a timing of executing the abnormality countermeasure mentioned above. Further, the "wear depth" mentioned above can be determined, for example, as shown in FIG. 4, on the basis of a predetermined wear area S in the lubricated portion, and the metal concentration (the wear volume) of the metal particle in the lubricating oil estimated in the manner mentioned above. Further, as the "emission spectrometry" mentioned above, there can be listed up, for example, an emission spectrometry analysis using an arc discharge, a spark discharge, an inductively coupled plasma and the like.

Further, the hole diameter of the "filter" mentioned above is preferably between 0.01 and 10.00 μm, more preferably between 0.05 and 5.00 μm, further preferably between 0.07 and 3.00 μm, and particularly preferably between 0.10 and 1.00 μm. Further, the "result of diagnosis" mentioned above may be constituted by an information, for example, relating to the wear aspect (the failure mode) in the lubricated portion such as the adhesive wear, the abrasive wear (the cutting wear), the fatigue wear and the like. Further, it may be an information relating to the cause of generation in correspondence to the various wear aspect, for example, the lack of oil film generating the adhesive wear, the external mixing foreign material and the wear particle generating the abrasive wear, the vibration and the overload generating the fatigue wear, and the like. Further, it may be an information relating to the abnormality countermeasure, for example, the lubricating oil filtration, the additive agent input, the additional oil, the shutdown, the overhaul, the parts replacement and the like. Further, it may be, for example, an information relating to a time of execution of the abnormality countermeasure mentioned above.

Further, the "method of diagnosing the lubricated portion" can diagnose a state of the lubricated portion on the basis of a combination of one or more of a size, a shape and a color of the metal particle in the lubricating oil obtained by a Ferrography method or can diagnose a state of the lubricated portion on the basis of the driving number of the driving mechanism in connection with the lubricated portion, in view of analyzing the lubricating oil multilaterally so as to improve an accuracy of diagnosis of the lubricated portion, for example, in addition to the metal concentration in the lubricating oil obtained by the emission spectrometry analysis. Further, the "system of diagnosing the lubricated portion" mentioned above can be provided with a transmitting means for transmitting the result of diagnosis obtained by the diagnosing means to the remote place via the network. Accordingly, it is possible to rapidly transmit the result of diagnosis to the remote place.

DESCRIPTION OF THE PREFERRED EMBODIMENT

A description will be particularly given below of an embodiment in accordance with the present invention with reference to the accompanying drawings. In this case, in the present embodiment, a lubricated portion is exemplified by a sliding bearing portion in a large-scaled equipment in an electric power plant. Further, in the present embodiment, a system of diagnosing mentioned below is placed in a predetermined analysis facility, and the analysis facility analyzes and diagnoses a lubricating oil picked up in the electric power plant or the like which are placed in a remote location.

(1) General Structure of System of Diagnosing Lubricated Portion

Figure 1:
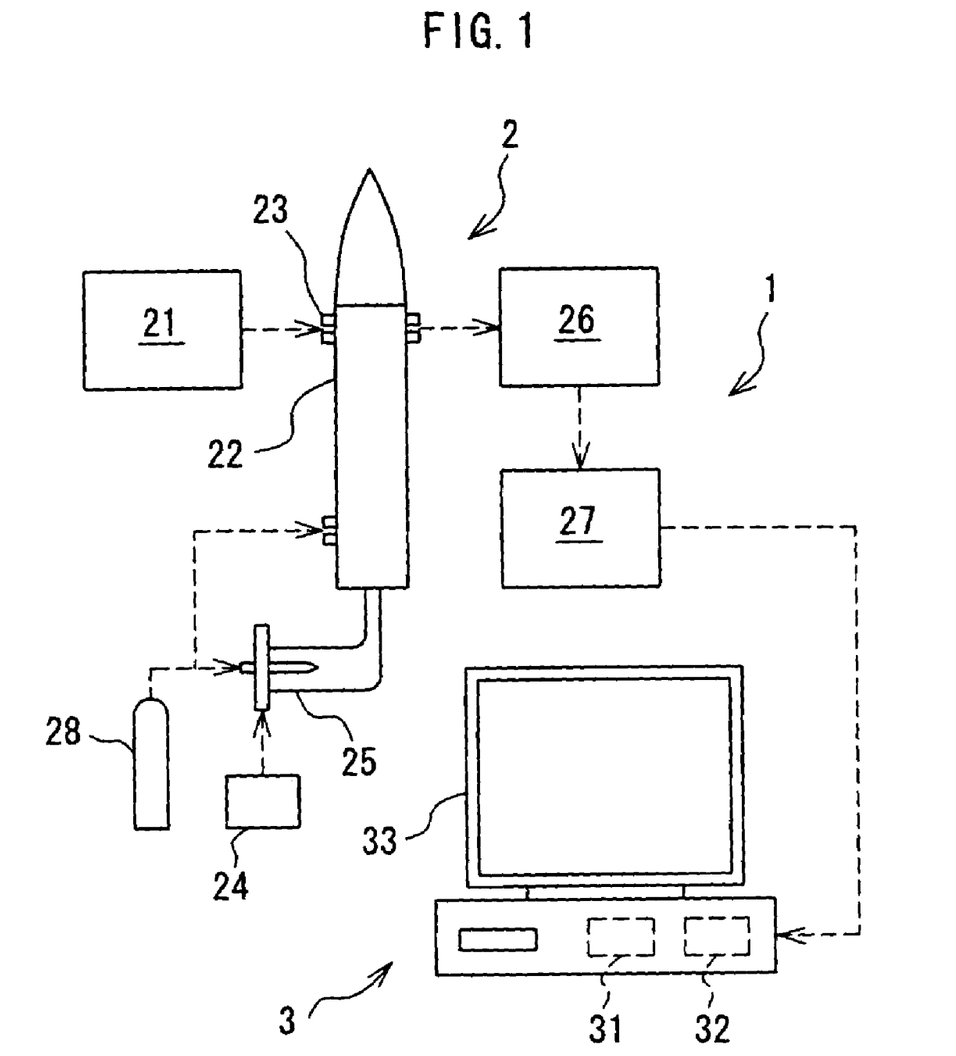
FIG. 1 is a schematic view for explaining a general structure of a system of diagnosing a lubricated portion.

A lubricated portion diagnosing system 1 in accordance with the present embodiment is basically provided with an inductively coupled plasma emission spectrometry apparatus 2 (hereinafter, also refer simply to an ICP emission spectrometry apparatus 2), and a computer 3, as shown in FIG. 1. The ICP emission spectrometry apparatus 2 is provided with a high frequency power source 21, a silica glass torch 22, an induction coil 23 wound around the torch 22, a sample container 24, a nebulizer 25, a spectroscope 26 and a data processing portion 27. Further, an argon gas fed from an argon gas bomb 28 into the torch 22 is excited by the induction coil 23, and a high temperature plasma is generated. Further, a sample oil within the sample container 24 is sucked up by a part of the argon gas fed to the nebulizer 25 so as to be introduced into the argon gas within the torch 22, and emits light. The luminescence is separated by the spectroscope 26, a luminescent strength of each of wavelengths is detected by a photomultiplier tube, and a gained electric signal is arithmetically processed by the data processing portion 27 so as to calculate the metal concentration. In this case, the data processing portion 27 mentioned above is structured such as to output a value of the calculated metal concentration to the computer 3, however, the structure is not limited to this, for example, the structure may be made such that the value of the metal concentration is sent and received via a recording medium such as a flexible disc or the like between the data processing portion 27 and the computer 3. Further, the metal concentration mentioned above may be constituted, for example, by a concentration of each of metal elements such as Fe, Pb, Cu, Zn, Ca, Mg and the like, or a concentration of an entire of the metal elements.

The computer 3 is provided with an operation portion 31 executing an arithmetic process, a display process and the like, and a memory portion 32 storing data in various processes. An wear depth of a sliding bearing portion mentioned below is calculated by the operation portion 31 on the basis of the value of the metal concentration input from the data processing portion 27, and the result of calculation is stored in the memory portion 32 (refer to step P2 in FIG. 3). Further, a rate of change of the wear depth in accordance with a time elapse is calculated by the operation portion 31 on the basis of the wear depths in this time and the preceding analyses and an analyzing time interval stored in the memory portion 32 (refer to step P3 in FIG. 3). Further, a state of the sliding bearing portion is diagnosed by the operation portion 31 on the basis of the rate of change mentioned above (refer to step P4 in FIG. 3), and the result of diagnosis is output and displayed to an output means such as a display monitor 33, a printer (not shown) and the like (refer to step P5 in FIG. 3).

Figure 5:
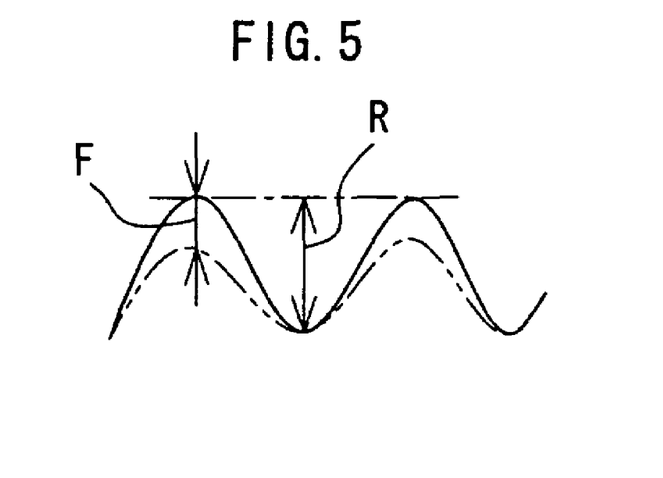
FIG. 5 is schematic views for explaining an wear depth (a surface roughness) of a sliding bearing portion.

In this case, the wear depth F is determined, for example, on the basis of a predetermined area S (an entire surface area in a side of bearing×⅓; shown by a diagonal line in the drawing) in the sliding bearing portion 4, and a metal concentration (a metal volume) in the lubricating oil measured by the ICP emission spectrometry apparatus 2, as shown in FIG. 4. In this case, as shown in FIG. 5, if the wear depth F approximately coincides with a surface roughness R of the new sliding bearing portion 4, a seizure is generated. Accordingly, it is desirable to execute a shutdown, an overhaul, a parts replacement and the like of a structure including the sliding bearing portion just before the seizure.

(2) Method of Diagnosing Lubricated Portion

Figure 2:
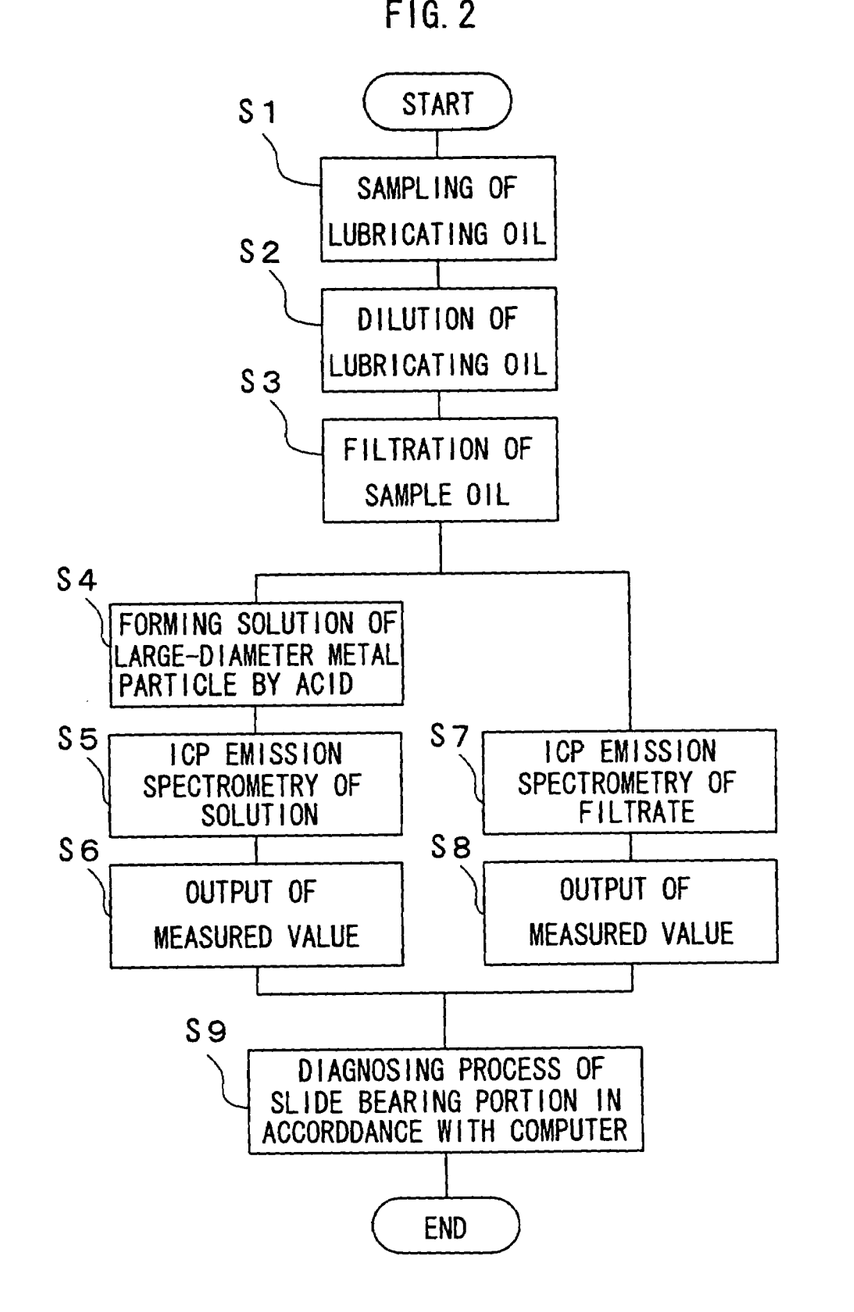
FIG. 2 is a flow chart for explaining a method of diagnosing a lubricated portion.
Figure 3:
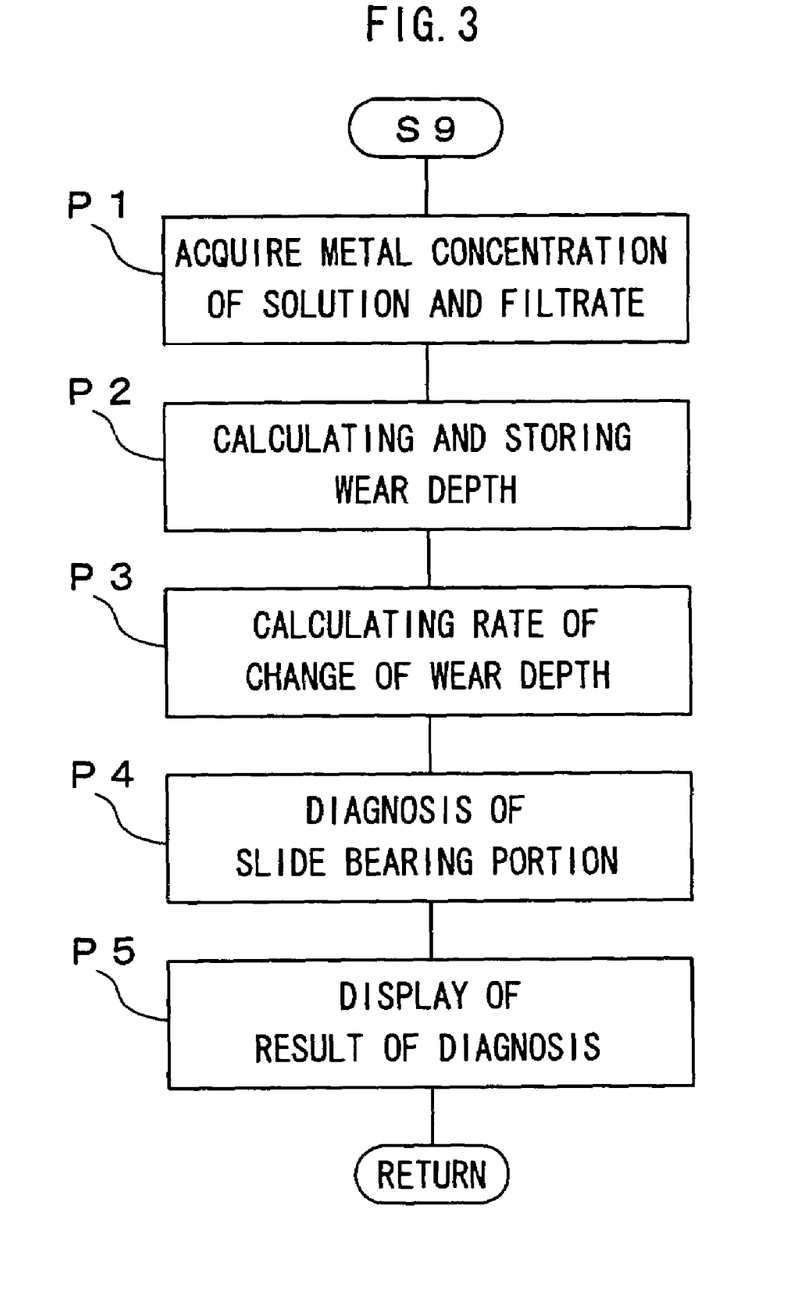
FIG. 3 is a flow chart for explaining a diagnosing process (step S9) in FIG. 2.

Next, a description will be given of a method of diagnosing a lubricated portion in accordance with the present embodiment with reference to flow charts in FIGS. 2 and 3. First, an operator samples a middle layer portion in the lubricating oil used in a plurality of sliding bearing portions 4 (step S1). Thereafter, 10 ml of the sampled lubricating oil is diluted by an organic solvent so as to obtain 100 ml of sample oil (step S2), and the sample oil is filtrated by a filter (not shown) having a hole diameter of 0.8 μm. Accordingly, a large-diameter metal particle (for example, an iron particle (powder)) having a particle diameter larger than 0.8 μm is separated from the sample oil, and a small-diameter metal particle, a dissolved metal, a metal additive agent and the like having a particle diameter equal to or smaller than 0.8 μm is included in the filtrate (step S3). Next, the separated large-diameter metal particle is dissolved by an aqua fortis so as to be brought into solution (step S4). Next, the solution is put into the sample container 24, the ICP emission spectrometry apparatus 2 is operated, and the metal concentration of the solution is measured in accordance with the ICP emission spectrometry (step S5), and a measured value (for example, 0.5 ppm) is output to the computer 3 by the data processing portion 27 (step S6). Further, approximately in the same manner as that of the solution mentioned above, the filtrate is put into the sample container 24, the ICP emission spectrometry apparatus 2 is operated, and the metal concentration of the filtrate is measured in accordance with the ICP emission spectrometry (step S7), and a measured value (for example, 5.0 ppm) is output to the computer 3 by the data processing portion 27 (step S8). Thereafter, the diagnosing process of the sliding bearing portion 4 is executed by the computer 3 (step S9).

Figure 6:
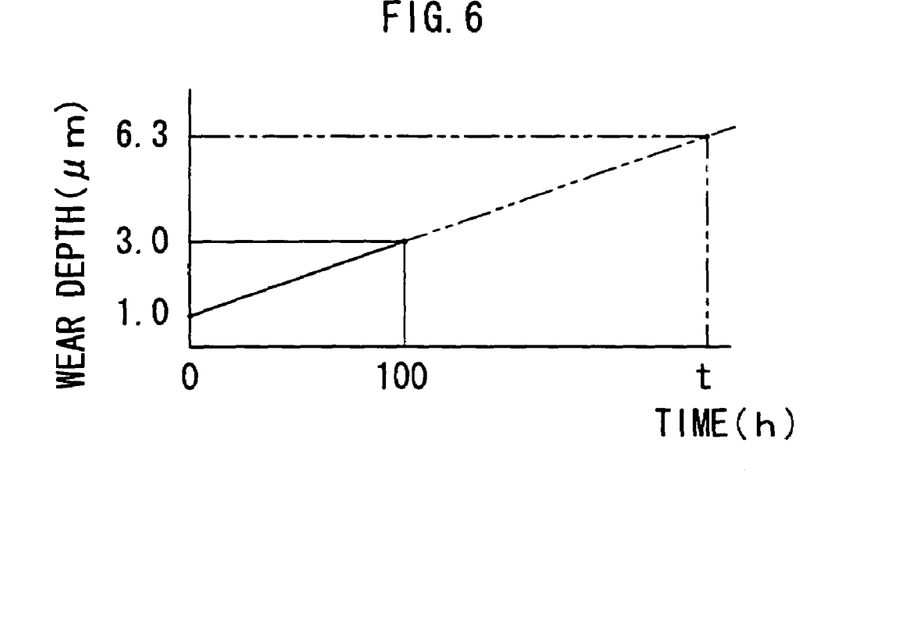
FIG. 6 is a schematic view for explaining a rate of change of an wear depth in accordance with a time elapse.

In the diagnosing process shown in the step S9 mentioned above, the computer 3 acquires and stores the measured value of the metal concentration of each of the solution and the filtrate from the data processing portion 27 (step P1). Thereafter, the wear depth F is calculated on the basis of the total value of the measured values, and is stored (step P2). Next, the rate of change of the wear depth F in accordance with the time elapse is calculated on the basis of the wear depth F (for example, 1 µm) stored in the preceding analysis, the wear depth F (for example, 3 µm) stored in this time analysis, and the analyzing time interval (for example, 100 hour) between the preceding and this time analyses (step P3; refer to FIG. 6). Next, the timing (for example, 165 hour later) just before the wear depth F reaches the predetermined surface roughness R (for example, 6.3 µm) of the sliding bearing portion 4, that is, the timing for the overhaul or the parts replacement is forecasted on the basis of the rate of change (step P4). Thereafter, a graph (refer to FIG. 6) showing a change of the wear depth F in accordance with the time elapse, a diagnosis comment (refer to FIG. 7) and the like are output and displayed as the result of diagnosis on the display monitor 33 or the like (step P5).

Figure 7:
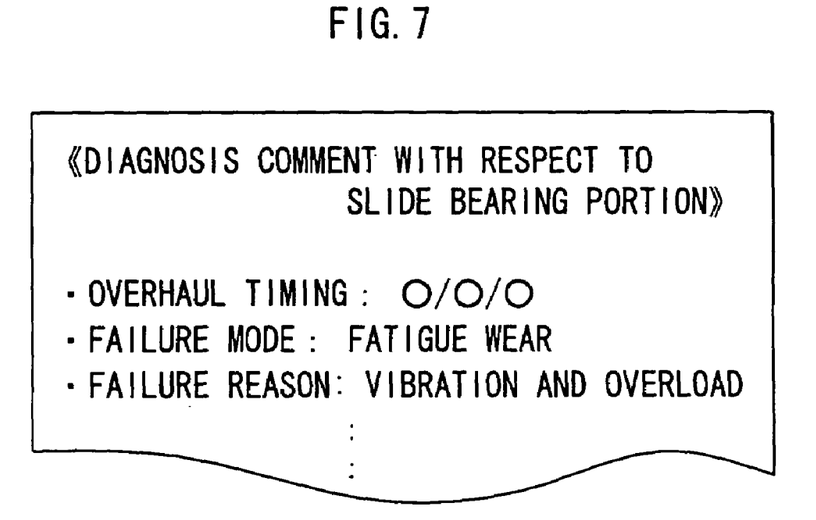
FIG. 7 is a schematic view for explaining one example of a diagnosis comment.

In this case, there are described information such as an overhaul timing, a failure mode, a failure reason and the like as the diagnosis comment mentioned above.

(3) Effect of Embodiment

As mentioned above, in accordance with the method of diagnosing the lubricated portion on the basis of the present embodiment, since the structure is made such that the sample oil is first filtrated by the filter so as to separate the large-diameter metal particle, the metal concentration of the solution in which the large-diameter metal particle is dissolved by the acid is thereafter measured in accordance with the emission spectrometry, and the metal concentration of the filtrate is measured, it is possible to measure the metal concentration of the solution in which the large-diameter metal particle is securely brought into solution by the acid even in the case that the large-diameter metal particle having the particle diameter larger than 10 µm exists in the lubricating oil, so that it is possible to precisely measure the metal concentration in the lubricating oil. As a result, it is possible to accurately diagnose the state of the lubricated portion on the basis of the accurate measured value of the metal concentration. Further, in the present embodiment, since the metal concentration of the lubricating oil is measured in accordance with the ICP emission spectrometry, it is possible to more precisely measure the metal concentration of a little amount of sample oil. Further, in the present embodiment, since the structure is made such that the rate of change of the wear depth F in accordance with the time elapse is determined on the basis of the precise measured value of the metal concentration, and the lubricated portion is diagnosed on the basis of the rate of change, it is possible to precisely control the tendency of the wear depth F and it is possible to accurately forecast the overhaul timing or the like of the lubricated portion.

Further, the lubricated portion diagnosing system 1 in accordance with the present embodiment is provided with the ICP emission spectrometry apparatus 2 and the computer 3, the ICP emission spectrometry apparatus 2 is provided with the data processing portion 27 outputting the measured value of the metal concentration to the computer 3, and the computer 3 is provided with the operation portion 31 which calculates the rate of change of the wear depth F in accordance with the time elapse on the basis of the measured value of the metal concentration, diagnoses the state of the lubricated portion on the basis of the result of calculation, and displays the result of diagnosis on the display monitor 33 or the like. Accordingly, it is possible to achieve an accurate automatic diagnosis of the state of the lubricated portion by executing the precise analysis of the lubricating oil and the tendency control of the wear depth F. Further, in accordance with the present embodiment, since the structure is made such as to display and output the graph showing the change of the wear depth F in accordance with the time elapse and the diagnosis comment, it is possible to easily and rapidly recognize the result of diagnosis.

In this case, the present invention is not limited to the embodiment mentioned above, and can employ various embodiments which are modified within the scope of the present invention in correspondence to the object and the intended use. In other words, the present embodiment is structured such that one ICP emission spectrometry apparatus 2 first measures the metal concentration of the solution in which the large-diameter metal particle is dissolved by the acid (steps S4 to S6 in FIG. 2), and thereafter measures the metal concentration of the filtrate (steps S7 and S8 in FIG. 2), however, the structure is not limited to this. For example, the structure may be made such that one ICP emission spectrometry apparatus first measures the metal concentration of the filtrate, and thereafter measures the metal concentration of the solution. Further, it is possible to simultaneously measure the metal concentrations of the filtrate and the solution by using two ICP emission spectrometry apparatuses. Further, in the present embodiment, there is exemplified the method of diagnosing the sliding bearing portion in the large-scaled equipment in the electric power plant and the system thereof, however, the structure is not limited to this. For example, the structure may be made as a method and system of diagnosing various portions to be lubricated in a machine tool, a construction machine, an aeronautical machine and the like. In particular, the structure may be particularly made as a method and system of diagnosing a sliding portion of a contact point switching mechanism in a transformer. Further, as the means for sending the result of diagnosis output by the computer to the electric power plant (remote place) in the diagnosing system in accordance with the present embodiment, it is possible to appropriately select from transmissions via a network such as a mailing, a facsimile, an internet, a telephone line and the like.

What is claimed is:

1. A method of diagnosing a lubricated portion comprising the steps of:

filtrating a lubricating oil picked up from the lubricated portion so as to separate a metal particle larger than a predetermined size and to form a filtrate;

thereafter measuring a metal concentration of a solution formed by dissolving said separated metal particle by an acid in accordance with an emission spectrometry and measuring a metal concentration of said filtrate in accordance with the emission spectrometry; and diagnosing a state of said lubricated portion on the basis of the respective metal concentrations of said solution and said filtrate.

2. A method of diagnosing a lubricated portion as claimed in claim 1, wherein the state of said lubricated portion is diagnosed by determining a wear depth in said lubricated portion from a total value of the respective metal concentrations of said solution and said filtrate, and on the basis of a rate of change of said wear depth in accordance with a time elapse.

3. A method of diagnosing a lubricated portion as claimed in claim 1, wherein said lubricating oil is filtrated by a filter having a hole diameter between 0.01 and 10.00 μm.

4. A method of diagnosing a lubricated portion as claimed in claim 1, wherein said emission spectrometry is constituted by an analyzing method using an inductively coupled plasma.

5. A system of diagnosing a lubricated portion comprising:

filtrating means for filtrating a lubricating oil picked up from the lubricated portion so as to separate a metal particle larger than a predetermined size and to form a filtrate;

emission spectrometry means for measuring respective metal concentrations of (1) a solution formed by dissolving said separated metal particle by an acid and (2) said filtrate;

diagnosing means for diagnosing a state of said lubricated portion on the basis of the respective metal concentrations of said solution and said filtrate; and display means for displaying a result of diagnosis of said diagnosing means.

6. A system of diagnosing a lubricated portion as claimed in claim 5, wherein the system of diagnosing the lubricated portion is provided with wear depth calculating means for determining a wear depth in said lubricated portion from a total value of the respective metal concentrations of said solution and said filtrate, memory means for storing the result of calculation by said wear depth calculating means, and change rate calculating means for determining a rate of change of said wear depth in accordance with a time elapse from the result of calculation by said wear depth calculating means and the result of storage by said memory means, and said diagnosing means diagnoses the state of said lubricated portion on the basis of the result of calculation of said change rate calculating means.

7. A system of diagnosing a lubricated portion as claimed in claim 5, wherein said filtrating means includes a filter having a hole diameter between 0.01 and 10.00 μm.

8. A system of diagnosing a lubricated portion as claimed in claim 5, wherein said emission spectrometry means is an emission spectrometry apparatus using an inductively coupled plasma.

9. A method of diagnosing a lubricated portion comprising the steps of:

filtrating a lubricating oil picked up from the lubricated portion so as to separate a metal particle larger than a predetermined size and to form a filtrate;

measuring a metal concentration of a solution formed by dissolving said separated metal particle by an acid, in accordance with an emission spectrometry and measuring a metal concentration of said filtrate in accordance with the emission spectrometry; and diagnosing a state of said lubricated portion of the basis of the respective metal concentrations of said solution and said filtrate, wherein the state of said lubricated portion is also diagnosed by determining a wear depth in said lubricated portion from a total value of the respective metal concentrations of said solution and said filtrate, and on the basis of a rate of change of said wear depth in accordance with a time elapse, and the timing before the wear depth of the lubricated portion reaches a predetermined surface roughness is forecast on the basis of the rate of change.

10. A system of diagnosing a lubricated portion comprising:

means for filtrating a lubricating oil picked up from the lubricated portion so as to separate a metal particle larger than a predetermined size and to form a filtrate ;

means for measuring respective metal concentrations of (1) a solution formed by dissolving said separated metal particle by an acid and (2) said filtrate;

means for calculating a wear depth in said lubricated portion from a total value of the respective metal concentrations of said solution and said filtrate;

means for storing the result of calculation by said wear depth calculating means:

means for calculating a rate of change of said wear depth in accordance with a time elapse from the result of calculation by said wear depth calculating means and the result of storage by said means for storing;

means for diagnosing a state of said lubricated portion on the basis of the reactive metal concentrations of said solution and said filtrate; and means for displaying a result of diagnosis of said diagnosing means, wherein said diagnosing means also diagnoses the state of said lubricated portion on the basis of the result of calculation of said change rate calculating means, and the timing before the wear depth of the lubricated portion reaches a predetermined surface roughness is forecast on the basis of the rate of change.

* * * * *